US007271003B2

(12) United States Patent
Tanaka et al.

(10) Patent No.: US 7,271,003 B2
(45) Date of Patent: Sep. 18, 2007

(54) RICE-DERIVED HIGH EXPRESSION POLYPEPTIDE CHAIN ELONGATION FACTOR PROMOTER AND METHOD OF USING THE SAME

(75) Inventors: Hiroshi Tanaka, Tsukuba (JP); Yasunori Ban, Tsukuba (JP); Toshiaki Kayano, Tsukuba (JP); Makoto Matsuoka, Nagoya (JP); Tomoaki Sakamoto, Tsukuba (JP)

(73) Assignee: National Insitute of Agrobiological Sciences, Ibaraki (JP)

( * ) Notice: Subject to any disclaimer, the term of this patent is extended or adjusted under 35 U.S.C. 154(b) by 480 days.

(21) Appl. No.: 10/473,493

(22) PCT Filed: Mar. 27, 2001

(86) PCT No.: PCT/JP01/02511

§ 371 (c)(1),
(2), (4) Date: Mar. 4, 2004

(87) PCT Pub. No.: WO02/077247

PCT Pub. Date: Oct. 3, 2002

(65) Prior Publication Data

US 2004/0133949 A1    Jul. 8, 2004

(51) Int. Cl.
*C07H 21/04* (2006.01)
*C12N 15/00* (2006.01)
*C12N 15/82* (2006.01)

(52) U.S. Cl. .................. 435/468; 435/320.1; 435/419; 800/287; 536/24.1

(58) Field of Classification Search ..................... None
See application file for complete search history.

(56) References Cited

FOREIGN PATENT DOCUMENTS

JP    10-248570 A    9/1998

OTHER PUBLICATIONS

Kim et al.,1994, Plant Molecular Biology 24: 105-117.*
Oommenn et al.,1994, The Plant Cell 6:1789-1803.*
Evans et al., 1992, Plant Mol. Biol. 20:1019-1028.*
Peng et al., 1995, Plant Mol. Biol. 27:91-104.*
Terui et al., A novel variant of translation elongation factor-1β: isolation and characterization of the rice gene encoding EF-1β2, *Biochem. Biophys. Acta*, 1442:369-372, (1998).
Matsumoto et al., "Cloning and characterization of the cDNA encoding rice elongation factor 1β", *FEBS Lett.*, 338(1):103-106, (1994).
McElroy et al., "Isolation of an Efficiant Actin Promoter for Use in Rice Transformation", *The Plant Cell*, 2:163-171, (1990).
EMBL database accession No. AP003261, *Oryza sativa* (japonica cultivar group), 2001.
GenBank database accession No. AQ259567, *Oryza sativa* (japonica cultivar group), 1998.
GenBank database accession No. AQ330640, *Oryza sativa* (japonica cultivar group), 1999.

* cited by examiner

*Primary Examiner*—Ashwin Mehta
*Assistant Examiner*—Li Zheng
(74) *Attorney, Agent, or Firm*—Perkins Coie LLP

(57) ABSTRACT

DNA having promoter activity for strongly expressing an exogenous gene specifically in plant tissue (particularly, tissue having active cell prolifaration) is provided. The DNA is a rice OsEF1β1 gene promoter which has a sequence indicated by SEQ ID NO. 1, or a portion of said sequence whose promoter activity is equivalent to that of said sequence indicated by SEQ ID No. 1. An expression vector containing the promoter and an exogenous gene expressibly linked to the promoter is also provided. A plant cell transformed with the expression vector, a plant regenerated from the plant cell, a progeny of the plant, a propagator of the plant, and a seed obtained from the progeny are also provided. A method for introducing an exogenous gene into plants using an expression vector is also provided.

9 Claims, 6 Drawing Sheets

FIG. 2A

Sequence of EF promoter region

```
gtcgacaaat aaccatatatt tactgttgat taccctgttg tcattattta ctgtaattt    60
attttaaaaa tggaggattt tcccatataa ctatataaac cgatgttcaa tgaccgaacg   120
aaaatgggaa aagtttcaaa aaggaaaaaa acttttcgcc ttcaaccggg cctaattcaa   180
aacagcccaa ctattttgcc tctgtttttt tacgtgattt ttcaaatgtt caatttcaaa   240
aaaaaaaggt caagttcaag cttgacatga atttttgacct tgttttttaca tgcatttaa  300
aatggaaact gaagttcaaa acataggggga gaaagcaata gcctagcaaa caaaaccatt  360
ttcccctcc  aattggacct aatttgaaac aacaccccaat tgaaaatgga atatgtctac  420
tttgactccc ttaactagtg tcttaaccta atttgtatct ttaaaccgta atagcggata   480
ttttgacccc caactattaa aactggtgta atttgtctcc ctcaacggtt ttggaggact   540
gttcactatc atggagcata cgtggcgggng ttgtaagcgt ctgtcgagga gtgatcctct  600
ctagcaggag atcgtgagac ccccctttcg tgagttcggc cggggaagaa gctcgcctct   660
agaaatcgcg tatccgtccc caaggctcct agctagctcg cacacaacca aattatacag   720
gttcgggccg ctatgaagcg taatacccta ctcctgtgta tgggatttag actgagagtt   780
acaatggttc ctaaactcgg gagaacactc ttacttccct cctccacaag ctcaggtttt   840
```

FIG.2B

```
ctgagagtcg tcctctttct cggtgggtaa ggtcctcctt ttatacctca aggggatacc    900
acatgcaccg cttctaccta ctcttttttc gggaggggac ccaccatatc ttgactggaa    960
ctcgacccgt gccttcgcct ggaagctaaa ccatagcttg tccttgagcg gggcccatca   1020
ccgtccctcg cctgacacgg gggacagccc tgtcattccc tcattaatag gtgaagactt   1080
gtggtggccg ccgtccgaat gaccccccga cgggacgggc catacctacc tccattccac   1140
cggaagcaga tgtgacgtgg gagcacggtt gtccatccag tcagacgtga ccggcgtcag   1200
ccggtcacag accggtcatt cttgaccatc gcgcgtcagt ttagcacgcc gcacgtctgc   1260
cccactgcat taaatgtgac atggggcagt tgaggcgctg tgcggattaa aggaagttca   1320
gcctggggcc cctcctcgct tgctcccccc gccaaacggc ggctgggcga gggcctcggg   1380
gcaaagcagt gcaagggccc gaggggcatg acgtggcacc ccgaggcccc gacacccgg   1440
ccgctcctgc ggttcgtgga atgcggggac aggaccatgc tgtagggaca cgtggtagga   1500
tggaaaggta gattcccctc acttcgcata cccccggcc catatctccg acagtttagg   1560
gcttagggtt taatagttgg agagtcgaga tatccggtac tgcgattcaa gcatacgaat   1620
```

FIG.2C

```
cagattcggc ccaataatcc agatgccaat aggacggccc atcaatccag ATGCAATACG    1680
ACGGCCCATC AGATCCCGTC CCCGAGAAGG AATCCCCCTC ACCGTTGGAT CCGATCCGAC    1740
GGCTGAGACC AGCCACACAA ACCCTCAATA TATATTCGCT CGCCCCCCGC TGCGTCTCGC    1800
CGCTCCTACA CCGCGCCGTC GCCAGCAGCC GCGCCGCTGC CTCTCCTCCT CCTCCCCTCG    1860
CCGCCGATCC AATCCGgtaa gcctgcccgc gaagctcccc tcgtccttcc ccggatagtt    1920
cgtcgcctcg tcaggcatct cgccgatttg gcgccgttct gttgttctgt ttggtggagc    1980
cgtgcgcgag atttccggtg tttgttgacc tgtttagctc tgatggattc accttgtgtt    2040
agttagtttt ccgtcgaatg gtgtggcgat taggtttggg gggattggtt cgtctgtgat    2100
tttgtagcta gatttttttga aatctagggt agtgtggagtg gggaagctgc tggccttagt    2160
ggatacatgc tgttcgtggt ctcctggttc ttgaaatcat gatgagttag tgctgtttga    2220
accttgaagc aaagttttaa gttattggag ttcctgtgct tagatttgta tactattagt    2280
gaagagatgc atagctgtac tgctgtagtg gatataggag tgttgttttt gattgctgg    2340
tgctcttcca tagcatccgg atgcggtgtt caattgtgta gttgtttatg tagttcaatg    2400
cactagaagc ttttattctt gaatgcctag ttattagttg ggtatgaagt ccaatgtgtg    2460
aaatgctgtc atgtttcaac tttagttaa gatatgaaac ttgagaaaca aatgaaaggt    2520
ttagattcag tactgatgta caacttaagt aacatctatg gttgtaaatt gtaccatgca    2580
ttggttattg tgaattagct cttttggttg attgaaacaa ttctctatgt gccaacagGT    2640
CACTTTCAGT C                                                        2651
```

US 7,271,003 B2

RICE-DERIVED HIGH EXPRESSION POLYPEPTIDE CHAIN ELONGATION FACTOR PROMOTER AND METHOD OF USING THE SAME

TECHNICAL FIELD

The present invention relates to breeding of useful plants using a plant gene promoter. More particularly, the present invention relates to breeding of useful plants using a promoter for rice polypeptide chain elongation factor β1 (hereinafter referred to as OsEF1β1).

BACKGROUND ART

In recent years, a method of introducing a gene of interest into plants and causing the gene to be expressed therein is becoming a generaly used means for conferring a desired trait to plants. However, such expression varies in the plant growth and development stages. For example, the gene is expressed in the young plant period, however, as the growth and development stages proceed, the expression may be attenuated. Therefore, there is a demand for a promoter for expressing an introduced gene in a stable manner regardless of the growth and development stages of plants.

Polypeptide chain elongation factors are involved in polymerization of amino acids by ribosome and are expressed in cells conducting protein synthesis. A chimeric gene in which the promoter region and 5' terminal region of a polypeptide chain elongation factor 1β (eEF-1β) is fused with a β-glucuronidase (GUS) gene was constructed in *Arabidopsis thaliana*. This chimeric gene was used to investigate the expression of the gene in transgenic plants (Gene, 170, (1996) 201–206). It was found that the first intron of the gene is required for a high level of expression. This experiment demonstrated that an enhancer-like element may be present in the first intron of the eEF-1β of *Arabidopsis thaliana*.

Studies of a rice polypeptide chain elongation factor were reported in FEBS Letters 311 (1992) 46–48, FEBS Letters 338 (1994) 103–106, and Biochemica et Biophysica Acta 1442 (1998) 369–372. FEBS Letters 311 (1992) 46–48 reported cloning and isolation of cDNA encoding the rice polypeptide chain elongation factor 1β' (EF-1β'). FEBS Letters 338 (1994) 103–106 reported cloning and isolation of cDNA encoding the rice polypeptide chain elongation factor 1β (EF-1β). Biochemica et Biophysica Acta 1442 (1998) 369–372 reported isolation and characterization of EF-1β 2 as a novel gene of a multigene family formed by rice polypeptide chain elongation factors 1β (EF-1β). However, these publications describe that the sequences of the above-described factors were only compared with the sequences of other members of the polypeptide elongation factor family. None of them mentions promoter activity.

Therefore, a promoter of a rice gene, which is permanent and highly active regardless of the growth and development stages of a plant and which is practically usable, will contribute to breeding of useful plants including crops, such as rice and the like, to a great extent.

DISCLOSURE OF THE INVENTION

The present invention relates to plant breeding using genetic engineering techniques. An object of the present invention is to provide a plant gene promoter capable of potently promoting expression in plant tissue, an expression vector containing the promoter, and a method using the promoter.

The present inventors found that a rice polypeptide chain elongation factor gene (OsEF1β1) has permanent, considerably high activity, and completed the present invention based on this finding.

The present invention provides DNA having promoter activity for strongly expressing an exogenous gene in plants. The DNA has a sequence indicated by SEQ ID NO. 1 (FIG. 2A to 2C), or a portion of the sequence whose promoter activity is equivalent to that of the sequence indicated by SEQ ID No. 1. The sequence indicated by SEQ ID NO. 1 contains a 5' region upstream of the rice OsEF1β1 structural gene, a first exon, a first intron, and a portion of a second exon. In one embodiment of this invention, the promoter may promote expression of the exogenous gene specifically in growth meristematic tissue of plants. In one embodiment of this invention, the DNA is hybridizable to the sequence indicated by SEQ ID NO. 1 or a portion thereof under stringent conditions.

The present invention provides an expression vector for strongly expressing an exogenous gene in plant tissue. The expression vector comprises a rice OsEF1β1 gene promoter, which has a sequence indicated by SEQ ID NO. 1 (FIG. 2A to 2C), or a portion of the sequence whose promoter activity is equivalent to that of the sequence indicated by SEQ ID No. 1. The expression vector further comprises an exogenous gene expressibly linked to the DNA. The present invention further provides a plant cell, transformed by the expression vector, which may be a monocotyledonous or dicotyledonous plant cell. The present invention provides a plant, regenerated from this plant cell, a progeny and a propagator of this plant, and a seed, obtained from this progeny.

The present invention further provides a method for introducing an exogenous gene into plants, in which the exogenous gene is desired to be expressed specifically in plants. This method comprises the steps of: transforming a plant cell with the above-described expression vector; and obtaining a plant by redifferentiation of the transformed plant cell. The plant cell may be a monocotyledonous or dicotyledonous plant cell.

BRIEF DESCRIPTION OF THE DRAWINGS

FIGS. 2A to 2C are diagrams showing the sequence of a 5' terminal region of OsEF1β1. In the figure, "n" indicates A, T, C or G. In the figure, bases in capital letters indicate an exon site (position 1671 to 1876 and position 2639 to 2651).

BEST MODE FOR CARRYING OUT THE INVENTION

Figure 1:
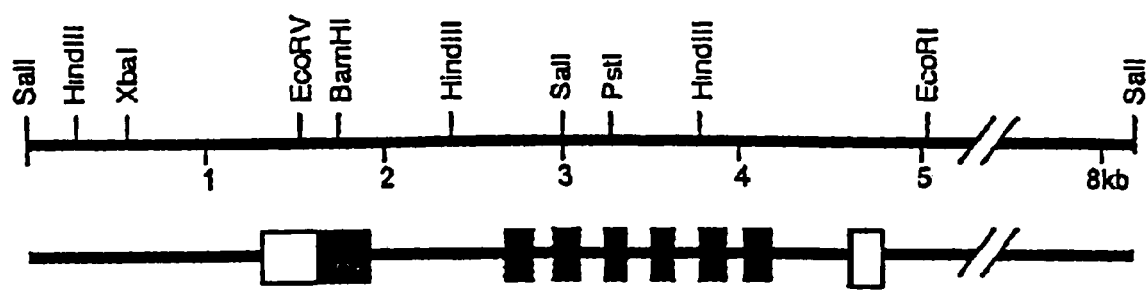
FIG. 1 shows a restriction map of a λOsEF1β1 insertion fragment.

Hereinafter, the present invention will be described in more detail.

(Isolation of a Rice OsEF1β1 Gene Promoter)

A rice OsEF1β1 gene promoter can be obtained by screening a rice genomic library. A rice genomic DNA library (Rice Genomic Library) commercially available from CLONTECH Laboratories Inc., Palo Alto, Calif. can be used.

As a probe for screening, rice OsEF1β1 cDNA which was isolated by the present inventors can be used.

Initially, *E. coli* is infected with a rice genomic gene library which is produced using phage λ, followed by formation of plaques. These plaques are transferred to a membrane, such as nitrocellulose or the like, in accordance with a commonly used method, followed by hybridization with labeled screening probes. After hybridization, the membrane is washed, followed by autoradiography. DNA is prepared from a phage for which hybridization is confirmed.

The prepared phage DNA is digested with a combination of appropriate restriction enzymes, and the resultant fragments are separated by agarose gel electrophoresis. The separated DNA fragments are transferred to a nylon membrane, followed by hybridization with the above-described screening probe. Screening is performed based on signal intensity and a band pattern difference.

It is believed that a clone having the most intense signal contains the OsEF1β1 gene, while clones having weaker signals contain a gene similar to, but not, OsEF1β1. Further, by comparing band patterns, it is possible to identify a clone lacking a part of the gene. Furthermore, by producing a physical map of each clone based on a band pattern thereof, it is possible to identify a clone having a 5' region of about 1.6 Kbp in length upstream of a structural gene, which is inferred to include a promoter.

In the above-described manner, the complete OsEF1β1 genomic gene can be isolated.

By comparing the base sequence of the OsEF1β1 genomic gene with the base sequence of OsEF1β1 cDNA, a promoter region can be identified. If the genomic gene has an intron, the promoter sequence may contain not only the 5' region upstream of the structural gene but also a region, such as a first intron or the like. This promoter sequence is preferably a sequence indicated by SEQ ID NO. 1 (see FIGS. 2A to 2C); in SEQ ID NO. 1 and the sequence shown in FIG. 2, "n" indicates any one of adenine (A), thymine (T), guanine (G) and cytidine (C)). The sequence indicated by SEQ ID NO. contains a 5' region upstream of the rice OsEF1β1 structural gene, a first exon, a first intron, and a second exon.

(Identification of an Active Portion of a Promoter by Measuring GUS Activity)

When the promoter region of the OsEF1β1 gene is specified, the sequence thereof can be excised and integrated into a plant expression vector. In order to assess the activity of the integrated promoter, a plasmid can be produced, in which a reporter gene, such as a gene encoding an appropriate enzyme, is linked downstream of the promoter. This plasmid is introduced into plant cells, and expression of the gene is observed by, for example, measuring enzyme activity. When plants are used as hosts, for example, it is usual to use a plasmid, such as pBI101 or the like, to carry out measurement with expression of β-glucuronidase (GUS) or the like as an indicator. This measurement method using GUS expression can be herein used.

GUS activity can be measured in accordance with a procedure described in, for example, Syokubutsu-saibo-kogaku [Plant Cell Engineering], Vol. 4, No. 4, pp. 281–286 (1992); op. cit., Vol. 5, No. 5, pp. 407–413 (1992); and Plant Mole. Biol. Reporter 5(4) 387–405 (1987). The measurement method is not so limited. Briefly, tissue or a section of a plant is immersed and incubated in histochemical substrate solution containing 1 mM 5-bromo-4-chloro-3-indolyl-β-D-glucuronide (X-Gluc), 7% (v/v) methanol, and 50 mM sodium phosphate buffer solution (pH 7.0) at a temperature and a time which are appropriate for progression of a reaction (e.g., at 37° C. for 30 minutes to 4 hours when a fusion gene of GUS and a CaMV promoter or the like is introduced). In order to prevent browning and GUS inactivation, a reducing agent, such as dithiothreitol (DTT) or the like, may be added. For example, 2 mM DTT may be added immediately after sectioning; (when sections are prepared) in the stage of embedding the section in agar; in the stage of slicing the section; or in deaerating the section under reduced pressure. 5 mM DTT may also be added in a GUS reaction at 37° C. Thereafter, the reaction is arrested by addition of ethanol, followed by decoloration. The resultant tissue or section is observed under a microscope or a stereomicroscope.

Various deletion mutants in the promoter region of the OsEF1β1 gene (e.g., the promoter region of the OsEF1β1 gene partially deleted into various lengths from the 5' upstream side) are fused with the GUS gene in a plasmid. This plasmid is used to measure promoter activity. As a result, a portion or the like essential for the promoter activity can be identified. A method for identifying such an active portion is known to those skilled in the art. Therefore, for example, a sequence which is obtained by removing a sequence unnecessary for the promoter region of the OsEF1β1 gene and has the same activity as that of the promoter of the OsEF1β1 gene, is within the scope of the present invention.

Once the promoter region of the OsEF1β1 gene and the active portion thereof are specified, the sequence thereof can be modified so as to improve the promoter activity and change the specificity for tissue in which expression is performed. For example, a sequence, which is obtained by partially modifying the promoter region of the OsEF1β1 gene or an active portion thereof and has activity equivalent to that before modification, is within the scope of the present invention.

The promoter region having the sequence of SEQ ID NO. 1 (FIGS. 2A to 2C) expresses activity strongly in plant tissue. Therefore, as used herein, "strong" promoter activity means that the intensity of activity is greater than the intensity of at least conventional promoters (e.g., the cauliflower mosaic virus (CaMV) 35S promoter, the nopaline synthase promoter, and the like), preferably at least two times greater than that, more preferably at least 5 times greater than that, and even more preferably 10 time greater than that. This intensity can be measured by a GUS activity measurement method.

The promoter of the present invention can promote specifically expression of an exogenous gene in the growth meristematic tissue of plants. As used herein, "specifically" promoting expression of an exogenous gene in growth meristematic tissue means that a gene of interest is more highly expressed in growth meristematic tissue than at least one of other tissues or organs in the same plant. "Growth meristematic tissue" refers to any tissue in which cell division is active and protein synthesis is at a high level. With the promoter of the present invention, an exogenous gene is strongly expressed in growing points, such as for example, stem apex and root tip. Typically, meristematic tissue at the highest portion of plants forms stems or leaves until a certain stage, elongating stems and expanding leaves.

The lowest portion of meristematic tissue forms only root for the entire life. Expression of an exogenous gene by the promoter of the present invention can be promoted in, particularly, meristematic tissue. Such expression specificity can be assessed by preparing a transformed plant under conditions as herein described in examples below.

The plant promoter of the present invention allows an exogenous gene to be consistently expressed regardless of the growth and development stages of plants. In other words, the exogenous gene is expressed throughout the vegetative growth period of plants. Such expression consistency can be assessed by preparing a transformed plant under conditions as herein described in examples below.

Therefore, the term "equivalent" in promoter activity indicates that the intensity of activity is substantially the same as the intensity of the activity of at least a promoter region as a reference, and meanwhile, the specificity of activity is substantially the same as the specificity of the activity of the promoter region as a reference. It should be noted that the term "equivalent" is not intended to exclude the case where the intensity and specificity of activity are clearly higher than those of a promoter region as a reference. "Having promoter activity equivalent to that of the sequence of SEQ ID NO. 1" indicates that, for example, when the GUS gene is expressed in protoplasts under conditions described below, the GUS activity is at least about 50%, preferably at least about 70%, and more preferably at least about 90% of the GUS activity of the sequence of SEQ ID NO. 1.

The scope of the present invention may encompass a sequence hybridizable to the promoter region of the OsEF1β1 gene or the activity portion thereof under stringent conditions. As used herein, "stringent hybridization conditions" or "stringency" refers to conditions in a range from about 5° C. to about 20° C. or 25° C. below the melting temperature ($T_m$) of the target sequence and a probe with exact or nearly exact complementarity to the target. As used herein, the melting temperature is the temperature at which a population of double-stranded nucleic acid molecules becomes half-dissociated into single strands. Methods for calculating the $T_m$ of nucleic acids are well known in the art (see, e.g., Berger and Kimmel, 1987, Methods In Enzymology, Vol. 152: Guide To Molecular Cloning Techniques, San Diego: Academic Press, Inc., and Sambrook et al., (1989) Molecular Cloning: A Laboratory Manual, 2nd Ed., Vols. 1–3, Cold Spring Harbor Laboratory, hereinafter referred to as "Sambrook", both incorporated herein by reference). As indicated by standard references, a simple estimate of the $T_m$ value may be calculated by the equation: $T_m=81.5+0.41$ (% G+C), when a nucleic acid is in aqueous solution at 1 M NaCl (see e.g., Anderson and Young, Quantitative Filter Hybridization in NUCLEIC ACID HYBRIDIZATION (1985)). Other references include more sophisticated computations which take structural as well as sequence characteristics into account for the calculation of $T_m$. The melting temperature of a hybrid (and thus the conditions for stringent hybridization) is affected by various factors, such as the length and nature (DNA, RNA, base composition) of the probe and the nature of the target (DNA, RNA, base composition, present in solution or immobilized, and the like), and the concentration of salts and other components (e.g., the presence or absence of formamide, dextran sulfate, polyethylene glycol). The effects of these factors are well known and are discussed in standard references in the art, see e.g., Sambrook, supra, and Ausubel et al., Current Protocols in Molecular Biology, Greene Publishing and Wiley-Interscience, New York (1997). Typically, stringent hybridization conditions are salt concentrations less than about 1.0 M sodium ion, typically about 0.01 to 1.0 M sodium ion at pH 7.0 to 8.3, and temperatures at least about 30° C. for short probes (e.g., 10 to 50 nucleotides) and at least about 60° C. for long probes (e.g., greater than 50 nucleotides). As noted, stringent conditions may also be achieved with the addition of destabilizing agents such as formamide, in which case lower temperatures may be employed. For example, when two polynucleotides are specifically hybridized with each other under stringent hybridization conditions, they are identified as having substantial sequence identity. As used herein, the terms "substantial identity", "substantial sequence identity" or "substantial similarity" refers to the degree of sequence similarity between two polynucleotides in the context of nucleic acid. Alternatively, substantial sequence identity is described as percent identity between two nucleotide (or polypeptide) sequences. When two sequences have at least about 60%, preferably at least about 70% identity, at least about 80% identity, or at least about 90% identity, at least about 95% or 98%–100% identity, they are considered to be substantially identical to each other. Another degree of sequence identity (e.g., "substantially" less than) can be characterized by hybridization under different stringency conditions. The percent identity of sequences (nucleotides or amino acids) is typically calculated by determining optimal alignment of two sequences, and then comparing the two sequences. For example, exogenous transcripts employed in protein expression may be described as having a particular percent identity or similarity when compared with a reference sequence (e.g., a corresponding endogenous sequence). Optimal alignment of sequences may be conducted by the homology alignment algorithm of Needleman and Wunsch (1970) J. Mol. Biol. 48:443, by the search for similarity methods of Pearson and Lipman (1988) Proc. Natl. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by inspection by the local homology algorithm of Smith and Waterman (1981) Adv. Appl. Math. 2:482. The best alignment (i.e., the highest percent identity is obtained) is selected from those obtained by various methods. Typically, these algorithms compare two sequences over a "comparison window" (usually at least 18 nucleotides long) to identify and compare local regions of sequence similarity, and therefore, enables small additions or deletions (i.e., gaps). Additions and deletions typically have a length of 20 percent or less as compared to reference sequences without an addition or a deletion. It is sometimes preferable to describe sequence identity between two sequences by referencing a particular length or region (e.g., two sequences may be described as having at least 95% identity over a length of at least 500 base pairs). Usually, the length is at least about 50, 100, 200, 300, 400, or 500 base pairs, amino acids, or other residues. A percent of sequence identity is calculated by comparing two sequences optimally aligned over a comparison region where the number of sites at which the same nucleic acid bases (e.g., A, T, C, G or U) occur in both sequences is determined to obtain the number of matching sites, and comparing it with the total number (or percent) of bases of a reference sequence or a comparison region. Another algorithm suitable for measurement of sequence similarity is a BLAST algorithm, which is described in Altschul (1990) J. Mol. Biol. 215:403–410; and Shpaer (1996) Genomics 38:179–191. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Extension of the word hits in each direction are halted when: the cumulative alignment score falls off by the unknown quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff (1992) Proc. Natl. Acad. Sci. USA 89: 10915–10919) alignments (B) of 50, expectation (E) of 10, M=5, N=−4, and a comparison of both strands. The term BLAST refers to a BLAST algorithm for statistically analyzing similarity between two sequences. See Karlin (1993) Proc. Natl. Acad. Sci. USA 90:5873–5787. One measure of similarity provided by the BLAST algorithm is the smallest sum probability (P(N)), which provides an indication of the probability by which a match between two nucleotide or amino acid sequences would occur by chance. Alternatively, another indication that two nucleic acid sequences are similar is that the polypeptide encoded by the first nucleic acid is immunologically cross reactive with the polypeptide encoded by the second nucleic acid.

(Construction of an Expression Cassette and an Expression Vector and Their Use)

The sequence of the promoter region of the OsEF1β1 gene having confirmed activity or an active portion thereof can be incorporated in an appropriate plant expression vector.

The plant expression vector of the present invention can be prepared using gene recombinant techniques well known to those skilled in the art. The plant expression vector is preferably constructed using pBI vectors, for example. The present invention is not so limited.

"Plant expression vector" refers to a nucleic acid sequence which is operatively linked with promoters, such as various regulatory elements, which regulates expression of a gene, in host cells. Preferably, such a vector may contain a plant gene promoter of the present invention, a terminator, and a drug resistance gene. The type of an expression vector and the type of a regulatory element(s) used may vary depending on the host cell, which is well known to those skilled in the art. The plant expression vector of the present invention may further contain a T-DNA region. The T-DNA region enhances the efficiency of gene introduction, particularly when Agrobacterium is used to transform plants. This expression cassette may further contain an appropriate selectable marker gene for a particular host organism to be used.

A "terminator" is a sequence which is located downstream of a region encoding a protein of a gene and which is involved in the termination of transcription when DNA is transcribed into mRNA, and the addition of a poly A sequence. It is known that a terminator contributes to the stability of mRNA, and has an influence on the amount of gene expression. Examples of such a terminator include, but are not limited to, a CaMV35S terminator and a terminator for the nopaline synthetase gene (Tnos).

"Drug resistance gene" desirably facilitates selection of a transformed plant. A neomycin phosphotransferase II (NP-TII) gene for conferring kanamycin resistance, and a hygromycin phosphotransferase gene for conferring hygromycin resistance can be used. The present invention is not so limited.

An exogenous gene, which is intended to be expressed, is expressibly linked to a 3' region downstream of the above-described promoter, such as a multiple cloning site, resulting in a recombinant plasmid. As used herein, "exogenous gene" refers to any gene which is an endogenous gene of rice or other plants other than the OsEF1β1 gene, or a foreign gene with respect to plants and whose gene product expression is desirable to plants, particularly plant tissue having active cell proliferation.

With the resultant recombinant plasmid, plant cells can be transformed. Transformation of plant cells can be conducted by any method known to those skilled in the art, such as a method using Agrobacterium, electroporation into protoplasts, or the like. For example, plant cell protoplasts can be prepared in accordance with a method described in Kyozuka et al., Mol. Gen. Genet. 206:408–413 (1987). An example of a transformation method using Agrobacterium, which is preferable for monocotyledonous plants, is a method developed by the present inventors, which is described in PCT/JP/03920. With this method, monocotyledonous plants can also be transformed more quickly and efficiently. Transformation methods for plants are not so limited.

Transformed plant cells can be regenerated by a commonly used method into transformed plant tissue, and further, a whole plant. In production of expression plasmids for transformation, the OsEF1β1 gene promoter can be incorporated into a binary vector which is expressible in both bacterium and plant hosts. Such a binary vector is well known to those skilled in the art. For example, when pBI vectors or the like (including an Agrobacterium expression system) are used, a system for infecting plants with microorganisms can be utilized. By using an appropriate expression vector, an exogenous gene of interest can be introduced into any transformable plant, including monocotyledonous plants (e.g., rice and the like) and dicotyledonous plants (e.g., tobacco and the like).

"Plant cell" may be any plant cell. A plant cell may be in any form of a culture cell, a culture tissue, a culture organ, or a whole plant, preferably a culture cell, a culture tissue, or a culture organ, and more preferably a culture cell. A plant species which can be used in a production method of the present invention may be any plant species into which a gene can be introduced.

Examples of types of plants that can be used in the manufacturing method of the present invention include plants in the families of Solanaceae, Poaceae, Brassicaceae, Rosaceae, Leguminosae, Cucurbitaceae, Lamiaceae, Liliaceae, Chenopodiaceae and Umbelliferae.

Examples of plants in the Solanaceae family include plants in the *Nicotiana, Solanum, Datura, Lycopersion* and *Petunia* genera. Specific examples include tobacco, eggplant, potato, tomato, chili pepper, and petunia.

Examples of plants in the Poaceae family include plants in the *Oryza, Hordenum, Secale, Saccharum, Echinochloa* and *Zea* genera. Specific examples include rice, barley, rye, barnyard grass, sorghum, and maize.

Examples of plants in the Brassicaceae family include plants in the *Raphanus, Brassica, Arabidopsis, Wasabia,* and

*Capsella* genera. Specific examples include Japanese white radish, rapeseed, *Arabidopsis thaliana*, Japanese horseradish, and shepherd's purse.

Examples of plants in the Rosaceae family include plants in the *Orunus, Malus, Pynus, Fragaria*, and *Rosa* genera. Specific examples include plum, peach, apple, pear, Dutch strawberry, and rose.

Examples of plants in the Leguminosae family include plants in the *Glycine, Vigna, Phaseolus, Pisum, Vicia, Arachis, Trifolium, Alphalfa*, and *Medicago* genera. Specific examples include soybean, adzuki bean, kidney bean, pea, fava bean, peanut, clover, and bur clover.

Examples of plants in the Cucurbitaceae family include plants in the *Luffa, Cucurbita*, and *Cucumis* genera. Specific examples include gourd, pumpkin, cucumber, and melon.

Examples of plants in the Lamiaceae family include plants in the *Lavandula, Mentha*, and *Perilla* genera. Specific examples include lavender, peppermint, and beefsteak plant.

Examples of plants in the Liliaceae family include plants in the *Allium, Lilium*, and *Tulipa* genera. Specific examples include onion, garlic, lily, and tulip.

Examples of plants in the Chenopodiaceae family include plants in the *Spinacia* genera. A specific example is spinach.

Examples of plants in the Umbelliferae family include plants in the *Angelica, Daucus, Cryptotaenia*, and *Apitum* genera. Specific examples include Japanese udo, carrot, honewort, and celery.

"Plants" on which a promoter of the present invention acts include any plant into which a gene can be introduced. "Plants" includes monocotyledonous and dicotyledonous plants. Such plants include any useful plants, particularly crop plants, vegetable plants, and flowering plants of garden varieties. Preferable plants include, but are not limited to, rice, maize, sorghum, barley, wheat, rye, barnyard grass, foxtail millet, asparagus, potato, Japanese white radish, soybean, pea, rapeseed, spinach, tomato, and petunia. The most preferable plant to which the present invention is applied is rice, particularly Japonica rice.

As described above, the OsEF1β1 gene promoter can strongly express an exogenous gene in plant tissue. Therefore, by using a transformant selectable marker gene as an exogenous gene, it is made easier to select a transformed plant. For example, when an exogenous gene encoding a toxic protein as an exogenous gene is used, it is possible to control pest insects feeding on stems and leaves. When a disease resistance gene is used as an exogenous gene, it is possible to obtain plants having excellent disease resistance. The present invention also encompasses preparation of any useful plant by utilizing gene expression specific to vegetative growth tissue. Examples of the gene expressed by the promoter of the present invention include any gene which is desired to be expressed in tissue having active cell profileration.

An action of the promoter of the present invention may be inherited by the primary generation of transformed plants as well as subsequent generations of the plants. The action of the promoter may be exhibited in the primary generation of transformed plants and subsequent generations of the plants, propagators thereof (e.g., pollen), and seed produced from the propagators. Inheritance of an introduced promoter gene into subsequent generations can be confirmed by Southern analysis using a sequence of the promoter of the present invention as a probe.

According to the present invention, use of a promoter from a rice gene, which has a high level of activity in plant tissue (particularly, growth meristematic tissue, tissue having active cell proliferation, and the like) is provided. Therefore, the present invention can be utilized in not only breeding of rice but also breeding of other various plants.

EXAMPLES

The present invention will be described in detail by way of examples. These examples are not intended to limit the present invention. Materials, reagents, and the like used in the examples are available from commercial sources unless otherwise mentioned.

Example 1

Isolation of Rice OsEF1β1 Genomic Gene: Screening a Genomic Library

In order to isolate a rice EF promoter, a known cDNA sequence (Matsumoto et al., supra) was used to synthesize a pair of primers and mRNA extracted from rice callus was used as a template to conduct RT-PCR, resulting in cDNA fragments. These PCR products were labeled with an isotope and used as probes to screen a genomic library (EMBL3 phage vector) which had been prepared by partially degrading Nipponbare Sam3A. *E. coli* (XLI Blue) was infected with the phage (EMBL3) using a commonly used method and allowed to form plaques. The plaques were transferred to a nylon membrane using a commonly used method. The membrane was subjected to hybridization with the above-described probe labeled with $^{32}P$ using a commonly used method (Molecular Cloning, 2nd Ed., its disclosure is herein incorporated by reference). After hybridization, the membrane was washed, followed by autoradiography. DNA was prepared from a phage for which hybridization had been confirmed.

The prepared phage DNA is digested with a combination of appropriate restriction enzymes, SalI, EcoRI, HindIII, BamHI, and XhoI, and the resultant fragments were separated by agarose gel electrophoresis. The separated DNA fragments are transferred to a nylon membrane, followed by hybridization with the above-described screening probe. The membrane was subjected to autoradiography using a commonly used method so that DNA fragments hybridizing to the probe were detected.

Screening was performed based on signal intensity and a band pattern difference. It was believed that a clone having the most intense signal contained the OsEF1β1 gene, while clones having weaker signals contained a gene similar to, but not, OsEF1β1. Further, by comparing band patterns, it is possible to identify a clone lacking a part of the gene. Furthermore, by producing a physical map of each clone based on a band pattern thereof, it is possible to specify a clone having a 5' region of about 1.6 Kbp in length upstream of a structural gene, which is inferred to include a promoter. The clone was designated λOsEF1β1. FIG. 1 shows a restriction map of a λOsEF1β11 insertion fragment. As seen from FIG. 1, seven exons are present in the λOsEF1β1 insert.

By detailed Southern analysis, analysis of partial base sequence, PCR analysis based on the base sequence of OsEF1β1 cDNA, and the like, a λOsEF1β11 clone having a gene corresponding to OsEF1β1 cDNA and a 5' region of about 1.6 Kbp in length upstream of the gene, which is deduced to be a promoter region, were obtained. The sequence thereof was shown in FIGS. 2A to 2C.

Example 2

Preparation of an Expression Vector Having an OsEF1β1 Gene Promoter

The expression vector containing a 5' terminal region of the OsEF1β1 gene obtained in Example 1 had a sequence of 2,651 bp. It was found that a first exon is present in position 1,671 to 1,876 of the sequence, a portion of a second exon is present in position 2,639 to 2,651, and a first intron is present in each exon (see SEQ ID NO. 1 and FIGS. 2A to 2C).

Figure 3:
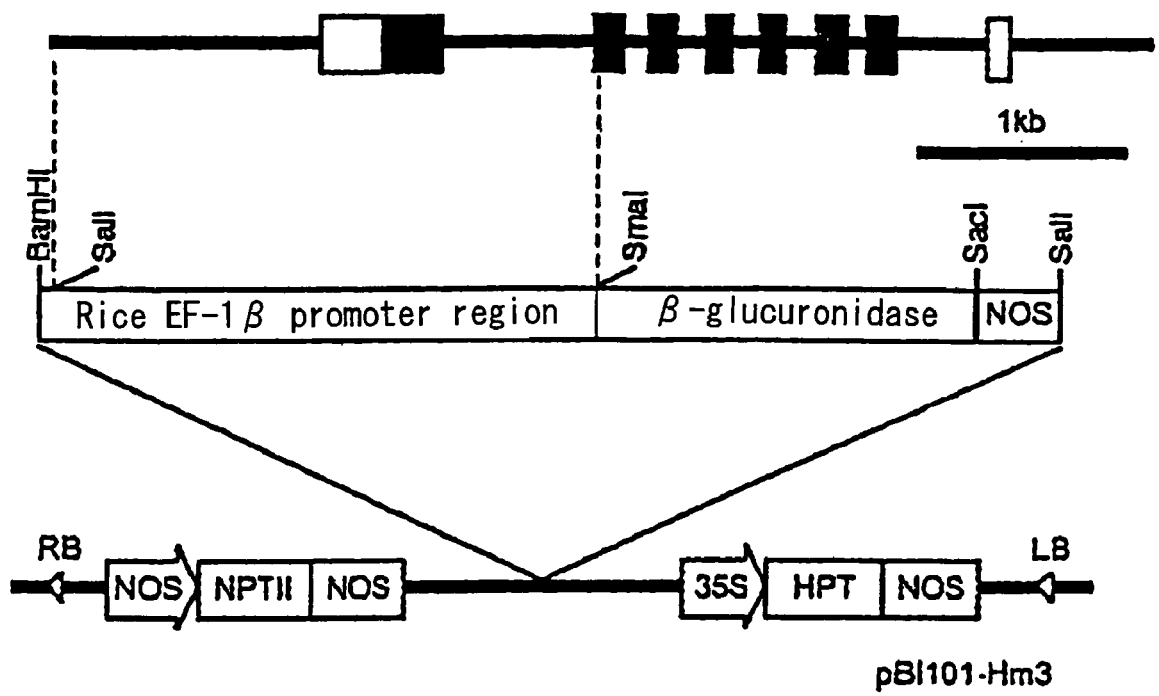
FIG. 3 is a schematic view showing an OsEF1β1:GUS fused construct.

FIG. 3 shows preparation of a vector having a rice OsEF1β1 gene promoter.

In order to obtain fragments which may contain a 5' nontranslational region of the rice OsEF1β1 gene, the clone λOsEF1β11 obtained in Example 1 was used (SalI (5' terminus) and SmaI (3' terminus). The fragment had the sequence of position 1 to 2,651 of the clone insertion sequence and contained a 5' nontranslational sequence, a first exon, a first intron, and a portion of a second exon. The function of the promoter of the OsEF1β1 gene was confirmed using a plant cell expression vector pBI101 (CLONTECH Laboratories Inc., Palo Alto, Calif.). This vector has a nopaline synthase promoter (NOS-Pro), a neomycin phosphotransferase II coding region (NPTII (KON R)) for conferring kanamycin resistance, a terminator for nopaline synthase (NOS-T), a β-glucuronidase (GUS) coding region, and a terminator for nopaline synthase (NOS-T) in this order. The above-described fragment was linked to the expression vector which had been restriction digested as described above, resulting in pBI101-Hm3 containing fusion with a GUS reporter gene. In this expression vector, the hygromycin phosphotransferase (HPT) gene (located between the cauliflower mosaic virus 35S (35S) and a terminator for the nopaline synthase gene (Tnos)) was also inserted downstream of the GUS coding region in order to confer hygromycin resistance.

Example 3

Transformation of Rice Seeds

Seeds of Nipponbare, which is a representative cultivar of rice, were immersed in 70% ethanol for 10 sec, where the seeds remained intact after removal of their chaff s. The seeds were washed with water, followed by immersion in an aqueous solution of 0.1% Tween20 and 2.5% sodium hypochlorite (NaClO) for 30 min, for sterilization. After thorough washing with water, the rice was subjected to the following sterile manipulations.

(Preculture)

The seeds were disseminated on 2,4-D containing N6D medium (30 g/l sucrose, 0.3 g/l casamino acid, 2.8 g/l proline, 2 mg/l 2,4-D, 4 g/l gel rite, pH5.8), and incubated for 5 days at 27° C. to 32° C. During this period of time, the seeds germinated.

(Plant Expression Vector)

*Agrobacterium* EHA101 was transformed with pBI101-Hm3 as prepared above (Hood et al., J. Bacteriol., 168: 1291–1301 (1986)). EHA101 is a bacterium in which the vir region of a helper plasmid is derived from potent pathogenic *Agrobacterium* A281. The *Agrobacterium* was cultured in AB medium supplemented with hygromycin (50 mg/l) (glucose (5 g/L), $K_2HPO_4$ (3 g/L), $NaH_2PO_4·2H_2O$ (1.3 g/L), $NH_4Cl$ (1 g/L), KCl (150 mg/L), $CaCl_2·2H_2O$ (10 mg/L), $F_2SO_4·7H_2O$ (2.5 mg/L), pH 7.2, bacto agar (1.5%)(3 g/200 ml), 1M $MgSO_4·7H_2O$ (120 µl/100 ml)) for 2 to 3 days at 25° C. in the dark.

(Infection with *Agrobacterium*)

The transformed *Agrobacterium* was suspended in AAM medium (AA-1 (×1000) 1 ml ($MnSO_4·4$–$6H_2O$ (1000 mg/100 ml), $H_3BO_3$ (300 mg/100 ml), $ZnSO_4·7H_2O$ (200 mg/100 ml), $Na_2MoO_4·2H_2O$ (25 mg/100 ml), $CuSO_4·5H_2O$ (2.5 mg/100 ml), $CoCl_2·6H_2O$ (2.5 mg/100 ml), KI (75 mg/100 ml)); AA-2 (×1000) 1 ml ($CaCl_2·2H_2O$ (15.0 g/100 ml)); AA-3 (×1000) 1 ml ($MgSO_4·7H_2O$ (25 g/100 ml)); AA-4 (×1000) 1 ml (Fe-EDTA (4.0 g/100 ml)); AA-5(× 1000) 1 ml ($NaH_2PO_4·2H_2O$ (15.0 g/100 ml)); AA-6 (×200) 5 ml (nicotinic acid (20 mg/100 ml); thiamine HCl (200 mg/100 ml), pyridoxine HCl (20 mg/ml), myo-inositol (2000 mg/100 ml)); AA-Sol (×100) 10 ml (L-arginine (5300 mg/300 ml), glycine (225 mg/300 ml)); AA-KCl (×50) 20 ml (KCl(3 g/20 ml)), casamino acid (500 mg/L); sucrose (68.5 g/L); glucose (36 g/L); L-glutamine (900 mg/L); L-aspartic acid (300 mg/L); pH 5.2) supplemented with 2 µg/ml acetosyringone. The above-described precultured seeds were immersed in this suspension for 90 seconds, and thereafter, transferred to 2N6-AS medium (30 g/l sucrose, 10 g/l glucose, 0.3 g/l casamino acid, 2 mg/12,4-D, 10 mg/l acetosyringone, 4 g/l gel rite, pH 5.2). Cocultivation was conducted in the dark for 3 days while incubating at 25° C.

(Removal of Bacteria and Screening)

After completion of cocultivation, the *Agrobacterium* was removed from the seeds by washing with N6D medium containing 500 mg/l carbenicillin. Thereafter, screening for transformed seeds was conducted under the following conditions.

First screening: the seeds were placed on N6D medium containing 2 mg/l 2,4-D, supplemented with carbenicillin (500 mg/l) and hygromycin (50 mg/l), and incubated at 30° C. for 7 days.

Second screening: the seeds were placed on N6D medium containing 2–4 mg/l 2,4-D, supplemented with carbenicillin (500 mg/l) and hygromycin (50 mg/l), and incubated at 30° C. for additional 7 days.

(Regeneration)

Selected transformed seeds were redifferentiated under the following conditions.

First redifferentiation: the selected seeds were placed on redifferentiation medium (MS medium (30 g/l sucrose, 30 g/l sorbitol, 2 g/l casamino acid, 2 mg/l kinetin, 0.002 mg/l NAA, 4 g/l gel rite, pH 5.8) supplemented with carbenicillin (500 mg/l) and hygromycin (25 mg/l)) at 30° C. for two weeks.

Second redifferentiation: the seeds were incubated at 30° C. for additional two weeks in redifferentiation medium identical to that which was used in the first redifferentiation.

(Potting)

The redifferentiated transformant was transferred to rooting medium (hormone-free MS medium supplemented with hygromycin (25 mg/l)). After the growth of roots was confirmed, the transformant was potted.

Example 4

Tissue Expression Observed by GUS Staining

In order to study gene expression by the rice OsEF1β1 gene promoter of the present invention in tissues of plants transformed by the vector having the promoter (rice about 6 weeks after dissemination), histochemical analysis of GUS activity was conducted. As a control, pBI121 containing the cauliflower mosaic virus (CaMV) 35S promoter, which is conventionally used as a plant expression promoter, was used to transform plants and gene expression by the promoters was compared with each other.

Histochemical analysis of GUS activity was conducted in order to study gene expression by the above-described promoter in plant tissue. Such histochemical analysis was conducted by a procedure described in Syokubutsu-saibo-kogaku [Plant Cell Engineering], Vol. 4, No. 4, pp. 281–286. This method is based on Jefferson et al. (EMBO J. 6:3901–3907(1987)) with improvements of Kosugi et al., Plant Science 70:133–140(1990). Briefly, an excised section was embedded in 5% (w/w) agar, and the agar block was sliced using a microslicer. Tissue slices having a thickness of 100 to 130 μm were immersed in histochemical substrate solution containing 1 mM 5-bromo-4-chloro-3-indolyl-β-D-glucuronide (X-Gluc), 7% (v/v) methanol, and 50 mM sodium phosphate buffer solution (pH 7.0), and incubated at 37° C. for 2–24 hours. 2 mM DTT was added immediately after sectioning; in the stage of embedding the section in agar; in the stage of slicing the section; or in the stage of deaerating the section under reduced pressure. 5 mM DTT was added in a GUS reaction at 37° C. Thereafter, the reaction was arrested by addition of ethanol, followed by decoloration. The slice was observed under a microscope.

Figure 4:
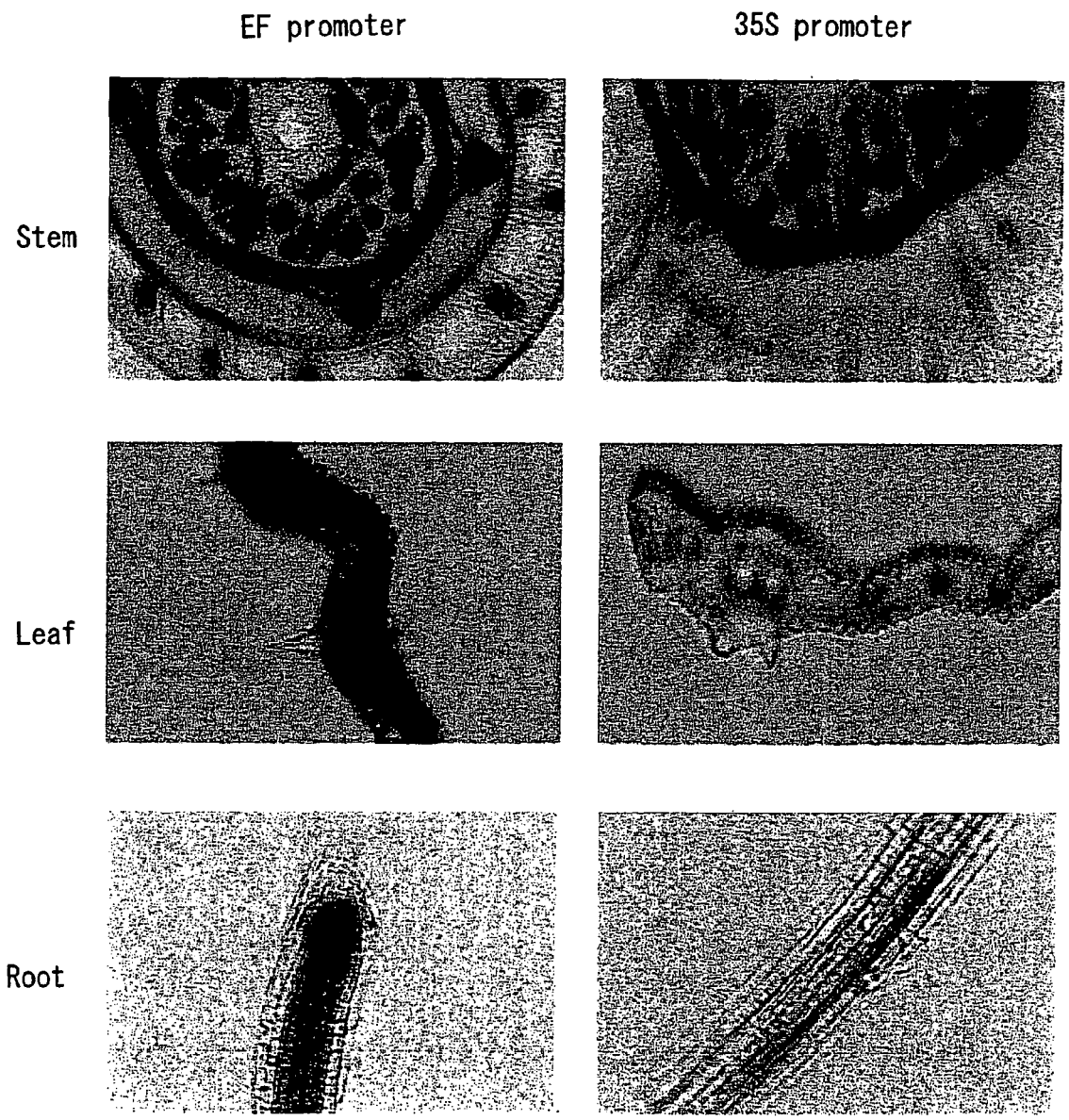
FIG. 4 is a photograph showing results of GUS histological staining of a transformed plant and a control plant transformed with a vector containing the 35S promoter as a promoter.

The results are shown in FIG. 4. To the left of FIG. 4, GUS activity in various tissues of plants transformed with the promoter of the present invention is shown. To the right of FIG. 4, GUS activity in various tissues of control plants is shown (stem, leaf, and root from the above). FIG. 3 shows that strong expression was exhibited in any of stem, leaf, and root of the transformed plant of the present invention, compared to the control plant. The GUS activity of the transformed plant of the present invention was about 5 times or more as strong as the GUS activity of the 35S promoter in the control plant. Moreover, in the transformed plant of the present invention, strong expression was observed in a portion near the center of the stem (vascular bundle), the base portion of the leaf, the end of the root. This shows that the promoter of the present invention is strongly expressed in, particularly, meristematic tissue.

INDUSTRIAL APPLICABILITY

The OsEF1β1 gene promoter of the present invention strongly promotes expression of a gene in plant tissue. Therefore, the present invention is useful for breeding of plants, such as rice and the like, by gene manipulation of the plants.

The invention claimed is:

1. An isolated DNA having promoter activity for expressing an exogenous gene in rice, wherein the DNA consists of the sequence indicated by SEQ ID NO: 1, or a portion of the sequence whose promoter activity is at least 50% of that of the sequence indicated by SEQ ID NO: 1 as assayed by GUS activity expressed in rice protoplasts.

2. The DNA according to claim 1, wherein the promoter promotes expression of the exogenous gene specifically in meristematic tissue.

3. An expression vector, comprising DNA according to claim 1 and an exogenous gene operably linked to the DNA.

4. A cell from rice, transformed by the expression vector according to claim 3.

5. A rice plant, regenerated from a plant cell according to claim 4.

6. A progeny of a plant according to claim 5, wherein said progeny comprises the expression vector of claim 3.

7. A propagator of the plant according to claim 5, wherein said propagator is pollen and said pollen comprises the expression vector of claim 3.

8. A seed, obtained from a progeny according to claim 6, wherein said seed comprises the expression vector of claim 3.

9. A method for introducing an exogenous gene into rice plants, wherein the exogenous gene is expressed in said rice plants, the method comprising the steps of:

transforming a cell from rice with the expression vector according to claim 3; and regenerating a transgenic rice plant from said transformed cells, wherein said exogenous gene is expressed in said transgenic rice plant.

* * * * *

SEQUENCE LISTING

```
<160> NUMBER OF SEQ ID NOS: 1

<210> SEQ ID NO 1
<211> LENGTH: 2651
<212> TYPE: DNA
<213> ORGANISM: Oryza sativa
<220> FEATURE:
<221> NAME/KEY: exon
<222> LOCATION: (1671)..(1876)
<220> FEATURE:
<221> NAME/KEY: exon
<222> LOCATION: (2640)..(2651)
<220> FEATURE:
<221> NAME/KEY: misc_feature
<222> LOCATION: 569
<223> OTHER INFORMATION: n= a, t, g, or c

<400> SEQUENCE: 1
gtcgacaaat aaccatattt tactgttgat taccctgttg tcattattta ctgtaatttt      60
attttaaaaa tggaggattt tcccatataa ctatataaac cgatgttcaa tgaccgaacg     120
aaaatgggaa aagtttcaaa aaggaaaaaa acttttcgcc ttcaaccggg cctaattcaa     180
aacagcccaa ctattttgcc tctgtttttt tacgtgattt ttcaaatgtt caatttcaaa     240
aaaaaaaggt caagttcaag cttgacatga attttgacct tgtttttaca tgcattttaa     300
aatggaaact gaagttcaaa acataggga gaaagcaata gcctagcaaa caaaaccatt     360
ttccccctcc aattggacct aatttgaaac aacacccaat tgaaatgga atatgtctac     420 tttgactccc ttaactagtg tcttaaccta atttgtatct ttaaaccgta atagcggata     480
ttttgacccc caactattaa aactggtgta atttgtctcc ctcaacggtt ttggaggact     540
gttcactatc atggagcata cgtggcggng ttgtaagcgt ctgtcgagga gtgatcctct     600
ctagcaggag atcgtgagac cccctttcg tgagttcggc cggggaagaa gctcgcctct     660
agaaatcgcg tatccgtccc caaggctcct agctagctcg cacacaacca aattatacag     720
gttcgggccg ctatgaagcg taataccta ctcctgtgta tgggatttag actgagagtt     780
```

```
acaatggttc ctaaactcgg gagaacactc ttacttccct cctccacaag ctcaggtttt    840
ctgagagtcg tcctctttct cggtgggtaa ggtcctcctt ttatacctca agggataccc    900
acatgcaccg cttctaccta ctcttttttc gggaggggac ccaccatatc ttgactggaa    960
ctcgacccgt gccttcgcct ggaagctaaa ccatagcttg tccttgagcg ggcccatca    1020 ccgtccctcg cctgacacgg gggacagccc tgtcattccc tcattaatag gtgaagactt    1080
gtggtggccg ccgtccgaat gaccccccga cgggacgggc catacctacc tccattccac    1140
cggaagcaga tgtgacgtgg gagcacggtt gtccatccag tcagacgtga ccggcgtcag    1200
ccggtcacag accggtcatt cttgaccatc gcgcgtcagt ttagcacgcc gcacgtctgc    1260
cccactgcat taaatgtgac atggggcagt tgaggcgctg tgcggattaa aggaagttca    1320
gcctggggcc cctcctcgct tgctcccccc gccaaacggc ggctgggcga gggcctcggg    1380
gcaaagcagt gcaagggccc gaggggcatg acgtggcacc ccgaggcccc gacaccccgg    1440
ccgctcctgc ggttcgtgga atgcggggac aggaccatgc tgtagggaca cgtggtagga    1500
tggaaaggta gattcccctc acttcgcata cccccgggcc catatctccg acagtttagg    1560
gcttagggtt taatagttgg agagtcgaga tatccggtac tgcgattcaa gcatacgaat    1620
cagattcggc ccaataatcc agatgccaat aggacggccc atcaatccag atg caa      1676
                                                          Met Gln
                                                              1 tac gac ggc cca tca gat ccc gtc ccc gag aag gaa tcc ccc tca ccg    1724
Tyr Asp Gly Pro Ser Asp Pro Val Pro Glu Lys Glu Ser Pro Ser Pro
        5                  10                  15 ttg gat ccg atc cga cgg ctg aga cca gcc aca caa acc ctc aat ata    1772
Leu Asp Pro Ile Arg Arg Leu Arg Pro Ala Thr Gln Thr Leu Asn Ile
     20                  25                  30 tat tcg ctc gcc ccc cgc tgc gtc tcg ccg ctc cta cac cgc gcc gtc    1820
Tyr Ser Leu Ala Pro Arg Cys Val Ser Pro Leu Leu His Arg Ala Val
 35                  40                  45                  50 gcc agc agc cgc gcc gct gcc tct cct cct cct ccc ctc gcc gcc gat    1868
Ala Ser Ser Arg Ala Ala Ala Ser Pro Pro Pro Pro Leu Ala Ala Asp
                 55                  60                  65 cca atc cg gtaagcctgc cgccgaagct cccctcgtcc ttccccggat agttcgtcgc    1926
Pro Ile Arg ctcgtcaggc atctcgccga tttggcgccg ttctgttgtt ctgtttggtg gagccgtgcg    1986
cgagatttcc ggtgtttgtt gacctgttta gctctgatgg attcaccttg tgttagttag    2046
ttttccgtcg aatggtgtgg cgattaggtt tgggggggatt ggttcgtctg tgattttgta    2106
gctagatttt ttgaaatcta gggtagtgtg agtggggaag ctgctggcct tagtggatac    2166
atgctgttcg tggtctcctg gttcttgaaa tcatgatgag ttagtgctgt ttgaaccttg    2226
aagcaaagtt ttaagttatt ggagttcctg tgcttagatt tgtatactat tagtgaagag    2286
atgcatagct gtactgctgt agtggatata ggagtgttgt ttttgatttg ctggtgctct    2346
tccatagcat ccggatgcgg tgttcaattg tgtagttgtt tatgtagttc aatgcactag    2406
aagcttttat ttctgaatgc ctagttatta gttgggtatg aagtccaatg tgtgaaatgc    2466
tgtcatgttt caacttttag ttaagatatg aaacttgaga aacaaatgaa aggtttagat    2526
tcagtactga tgtacaactt aagtaacatc tatggttgta aattgtacca tgcattggtt    2586
```

```
attgtgaatt agctcttttg gttgattgaa acaattctct atgtgccaac agg tca      2642
                                                           Ser
                                                           70 ctt tca gtc                                                         2651
Leu Ser Val
```